(12) United States Patent
Yan et al.

(10) Patent No.: US 8,895,072 B2
(45) Date of Patent: Nov. 25, 2014

(54) QUANTUM DOT BARCODE STRUCTURES AND USES THEREOF

(75) Inventors: Hao Yan, Chandler, AZ (US); Qiangbin Wang, Suzhou (CN); Yan Liu, Chandler, AZ (US)

(73) Assignee: Arizona Board of Regents, a body corporate of the State of Arizona Acting for and on Behalf of Arizona State University, Scottsdale, AZ (US)

( * ) Notice: Subject to any disclaimer, the term of this patent is extended or adjusted under 35 U.S.C. 154(b) by 1237 days.

(21) Appl. No.: 12/374,226

(22) PCT Filed: Sep. 11, 2007

(86) PCT No.: PCT/US2007/078114
§ 371 (c)(1),
(2), (4) Date: May 19, 2009

(87) PCT Pub. No.: WO2008/033804
PCT Pub. Date: Mar. 20, 2008

(65) Prior Publication Data
US 2009/0297448 A1   Dec. 3, 2009

Related U.S. Application Data

(60) Provisional application No. 60/843,621, filed on Sep. 11, 2006.

(51) Int. Cl.
| | | |
|---|---|---|
| *A61K 9/16* | (2006.01) | |
| *A61K 9/50* | (2006.01) | |
| *C09C 1/24* | (2006.01) | |
| *A61K 9/14* | (2006.01) | |
| *B82Y 10/00* | (2011.01) | |
| *B82Y 15/00* | (2011.01) | |
| *G01N 33/543* | (2006.01) | |
| *G01N 33/58* | (2006.01) | |
| *H01L 29/12* | (2006.01) | |

(52) U.S. Cl.
CPC ... *C09C 1/24* (2013.01); *A61K 9/14* (2013.01); *B82Y 10/00* (2013.01); *B82Y 15/00* (2013.01); *G01N 33/54366* (2013.01); *G01N 33/588* (2013.01); *C01P 2004/03* (2013.01); *C01P 2004/04* (2013.01); *C01P 2006/42* (2013.01); *H01L 29/127* (2013.01)
USPC ......................................................... 424/490

(58) Field of Classification Search
CPC ............. A61K 9/14; B82Y 5/00; B82Y 15/00
USPC ......................................................... 424/490
See application file for complete search history.

(56) References Cited

U.S. PATENT DOCUMENTS

| 6,597,010 B2 | 7/2003 | Eriksson et al. | |
| 6,680,211 B2 * | 1/2004 | Barbera-Guillem et al. | . 436/533 |

(Continued)

FOREIGN PATENT DOCUMENTS

WO   WO 2005015213 A1 *  2/2005

OTHER PUBLICATIONS

Alivasatos, 1996. Science 271:933-937.

(Continued)

*Primary Examiner* — Benjamin Packard
(74) *Attorney, Agent, or Firm* — McDonnell Boehnen Hulbert & Berghoff LLP (57) ABSTRACT

The present invention provides novel barcode microstructures and methods for making and using the microstructures for molecular recognition, and/or delivery of therapeutic, diagnostic, contrast, and imaging agents.

21 Claims, 3 Drawing Sheets

(56) References Cited

U.S. PATENT DOCUMENTS

| | | |
|---|---|---|
| 6,774,361 B2 | 8/2004 | Bawendi et al. |
| 6,924,160 B2 | 8/2005 | Wei et al. |
| 2003/0082237 A1 | 5/2003 | Cha et al. |

OTHER PUBLICATIONS

Salabas and Schüth F 2007 Magnetic Nanoparticles: Synthesis, Protection, Functionalization, and Application Angew. Chem. Int. Ed. 46 1222-44.
Gao, et al, 2004 Nature Biotechnology, 22, 969-976.
Nicewarner-Pena S R, Freeman R G, Reiss B D, He L, Pen D J, Walton I D, Cromer R, Keating C D and Natan M J 2001 Submicrometer metallic barcodes Science 294 137-41.
Han M, Gao X, Su J Z and Nie S 2001 Quantum-dot-tagged microbeads for multiplexed optical coding of biomolecules Nat. Biotechnol. 19 631-5.
Hill H D and Mirkin C A 2006 The bio-barcode assay for the detection of protein and nucleic acid targets using DTT-induced ligand exchange Nat. Protocols 1 324-36.
Pierce S E, Fung E L, Jaramillo D F, Chu A M, Davis R W, Nislow C and Giaever G 2006 A unique and universal molecular barcode array Nat. Methods 3 601-3.
Kuang M, Wang D, Bao H, Gao M, Moehwald H and Jiang M 2005 Fabrication of multicolor-encoded microspheres by tagging semiconductor nanocrystals to hydrogel spheres Adv. Mater. 17 267-70.
Xu H, Sha M Y, Wong E Y, Uphoff J, Xu Y, Treadway J A, Truong A, O'Brien E, Asquith S, Stubbins M, Spurr N K, Lai E H and Mahoney W 2003 Multiplexed SNP genotyping using the QbeadTM system: a quantum dot-encoded microsphere-based assay Nucleic Acids Res. 31(8) e43.
Li Y, Cu Yen T H and Luo D 2005 Multiplexed detection of pathogen DNA with DNA-based fluorescence nanobarcodes Nat. Biotechnol. 23 885-9.
Medintz I L, Uyeda H T, Goldman E R and Mattoussi H 2005 Quantum dot bioconjugates for imaging, labeling and sensing Nat. Mater. 4 435-46.
Mornet S, Vasseur S, Grasset F and Duguet E 2004 Magnetic nanoparticle design for medical diagnosis and therapy J. Mater. Chem. 14 2161-75.
Kettering M, Winter J, Zeisberger M, Bremer-Streck S, Oehring H, Bergemann C, Alexiou C, Hergt R, Halbhuber K J, Kaiser W A and Hilger I 2007 Magnetic nanoparticles as bimodal tools in magnetically induced labeling and magnetic heating of tumor cells: an in vitro study Nanotechnology 18 175101/1-9.
Hong X, Gao X and Jiang L 2007 Application of superhydrophobic surface with high adhesive force in no lost transport of superparamagnetic microdroplet J. Am. Chem. Soc. 129 1478-9.
Lu A-H, Salabas E L and Schlith F 2007 Magnetic Nanoparticles: Synthesis, Protection, Functionalization, and Application Angew. Chem. Int. Ed. 46 1222-44.
Selvan S T, Bullen C, Ashokkumar M and Mulvaney P 2001 Synthesis of Tunable, Highly luminescent QD-glasses through sol-gel processing Adv. Mater. 13 985-8.
Trau M and Battersby B J 2001 Novel colloidal materials for high-throughput screening applications in drug discovery and genomics Adv. Mater. 13 975-9.
Chan Y, Zimmer J P, Stroh M, Steckel J S, Jain R K and Bawendi M G 2004 Incorporation of luminescent nanocrystals into monodisperse core-shell silica microspheres Adv. Mater. 16 2092-7.
Selvan S T, Tan T and Ying J Y 2005 Robust, Non-Cytotoxic, Silica-coated CdSe quantum dots with efficient photoluminescence Adv. Mater. 17 1620-5.
Xu H, Cui L, Tong N and Gu H 2006 Development of high magnetization Fe3O4/polystyrene/silica nanospheres via combined miniemulsion/emulsion polymerization J. Am. Chem. Soc. 128 15582-3.

Lu Y, Yin Y, Mayers B T and Xia Y 2002 Modifying the surface properties of superparamagnetic iron oxide nanoparticles through a sol-gel approach Nano Lett. 2 183-6.
Salgueiriño-Maceira V, Correa-Duarte M A, Spasova M, Liz-Marzán L M and Farle M 2006 Composite silica spheres with magnetic and luminescent functionalities Adv. Funct. Mater. 16 509-14.
Wang D, He J, Rosenzweig N and Rosenzweig Z 2004 Superparamagnetic Fe2O3 beads-CdSe/ZnS quantum dots core-shell nanocomposite particles for cell separation Nano Lett. 4 409-13.
Kim J, Lee J E, Lee J, Yu J H, Kim B C, An K, Hwang Y, Shin C H, Park J G, Kim J and Hyeon T 2006 Magnetic fluorescent delivery vehicle using uniform mesoporous silica spheres embedded with monodisperse magnetic and semiconductor nanocrystals J. Am. Chem. Soc. 128 688-9.
Yi D, Selvan S T, Lee S, Papaefthymiou G C, Kundaliya D and Ying J Y 2005 Silica-coated nanocomposites of magnetic nanoparticles and quantum dots J. Am. Chem. Soc. 127 4990-1.
Sathe T R, Agrawal A and Nie S 2006 Mesoporous silica beads embedded with semiconductor quantum dots and iron oxide nanocrystals: dual-function microcarriers for optical encoding and magnetic separation Anal. Chem. 78 5627-32.
Mamedov A, Belov A, Giersig M, Mamedova N and Kotov N A 2001 Nanorainbows: graded semiconductor films from quantum dots J. Am. Chem. Soc. 123 7738-9.
Kagan C R, Murray C B, Nirmal M and Bawendi M G 1996 Electronic energy transfer in CdSe quantum dot solids Phys. Rev. Lett. 76 1517-20.
Franzl T, Klar T A, Schietinger S, Rogach A L and Feldmann J 2004 Exciton recycling in graded gap nanocrystal structures Nano Lett. 4 1599-603.
Brinker C Y and Scherer G W 1990 Sol Gel Science: the Physics and Chemistry of Sol-Gel Processing Academic Press Boston, p. 453-513.
Wang Q, Iancu N and Seo D K 2005 Preparation of large transparent silica monoliths with embedded photoluminescent CdSe@ZnS core/shell quantum dots Chem. Mater. 17 4762-4.
Wang Q, Xu Y, Zhao X, Chang Y, Liu Y, Jiang L, Sharma J, Seo D K and Yan H 2007 A facile one-step in situ functionalization of quantum dots with preserved photoluminescence for bioconjugation J. Am. Chem. Soc. 129 6380-1.
Iancu N, Sharma R and Seo D K 2004 Low-temperature synthetic method for size-controlled CdSe nanocrystals: utilization of boron selenide Chem. Comm. 20 2298-9.
Wang Q and Seo D K 2006 Synthesis of deep-red-emitting CdSe quantum dots and general non-inverse-square behavior of quantum confinement in CdSe quantum dots Chem. Mater. 18 5764-7.
Van Blaaderen A and Vrij A 1992 Synthesis and characterization of colloidal dispersions of fluorescent, monodisperse silica spheres Langmuir 8 2921-31.
Wang Q, Wei Q and Gu H 2003 Preparation of nano Fe3O4/polystyrene composite microspheres by in situ polymerization J. Chem. Eng. Jpn. 36 1227-30.
Wu P, Zhu J and Xu Z 2004 Template-assisted synthesis of mesoporous magnetic nanocomposite particles Adv. Funct. Mater. 14 345-51.
Lin Y W, Tseng W L and Chang H T 2006 Using a layer-by-layer assembly technique to fabricate multicolored-light-emitting films of CdSe@CdS and CdTe quantum dots Adv. Mater. 18 1381-6.
Gong Y, Gao M, Wang D and Mohwald H 2005 Incorporating fluorescent CdTe nanocrystals into a hydrogel via hydrogen bonding: toward fluorescent microspheres with temperature-responsive properties Chem. Mater. 17 2648-53.
Petruska, M. A.; Malko, A. V.; Voyles, P. M.; Klimov, V. I. Adv. Mater. 2003, 15, 610.
Wang, Q.; Wei, Q.; Gu, H. J. Chem. Ind. Eng. 2002, 53, 219.

* cited by examiner

QUANTUM DOT BARCODE STRUCTURES AND USES THEREOF

CROSS REFERENCE

This application claims priority to U.S. Provisional Patent Application Ser. No. 60/843,621 filed Sep. 11, 2006, incorporated by reference herein in its entirety.

STATEMENT OF GOVERNMENT SUPPORT

This was supported by grants from the National Science Foundation CCF-0453685, CCF-0453686, CTC-0545652. Thus, the U.S. government has certain rights in the invention.

BACKGROUND OF INVENTION

Current research in genomics, proteomics and personalized medicine requires fast, precise and high-throughput target profiling. To meet this challenge, barcode technology for massively parallel and high-throughput bio-detection has attracted much attention. Furthermore, multifunctional carriers are badly needed in the areas of disease diagnostics and therapy.

Fluorescently-labeled molecules have been used for a wide range of applications. Typically organic dyes are bonded to a probe, which in turn selectively binds to a target molecule. Then the target molecule is identified by exciting the dye molecule, causing it to fluoresce. However, there are many disadvantages to using an organic dye for these fluorescent-labeling systems. The organic dye has a broad emission spectrum (about 100 nm) and broad tails of emission at red wavelengths (about another 100 nm), which results in a severe limitation on the number of different color organic dye molecules which can be simultaneously or sequentially utilized for assays or diagnostics. Organic dyes also often have a narrow absorption spectrum (about 30-50 nm), thus requiring either multiple wavelength probes, or else a broad spectrum excitation source, for sequential excitation of a series of probes respectively excited at different wavelengths. Organic dyes also generally lack photostability, often bleaching or ceasing to fluoresce under repeated excitation.

Semiconducting quantum dots (QDs) have numerous advantages over organic dyes, such as high quantum yield, high molar extinction coefficients (~10-100× that of organic dyes), broad absorption with narrow, symmetric photoluminescence (PL) spectra (full-width at half-maximum ~25-40 nm) panning the UV to near-infrared, large effective Stokes shifts, high resistance to photobleaching and exceptional resistance to photo- and chemical degradation. Han et al. (*Nat. Biotechnol.* 19 631-5) disclosed a porous polymer for multiplexed detection, in which the QDs were embedded in swollen polymer beads. However, embedding does not permit precise control of QD position in the bead; thus the embedded QDs can aggregate and couple with each other inside the beads, which could cause spectral broadening, wavelength shifting, and/or energy transfer. In addition, the poor water-solubility of the polymer bead limits its biological applications.

SUMMARY OF THE INVENTION

In a first aspect the present invention provides a microstructure comprising:
(a) a core; and
(b) a plurality of distinct layers surrounding the core; wherein the plurality of distinct layers comprises (i) quantum dot-containing layers, and (ii) spacer layers not containing quantum dots, wherein there are at least two quantum dot containing layers; wherein the quantum dots are present in each quantum dot containing layer at a defined intensity level, wherein each quantum dot containing layer comprises a single type of quantum dot that is different relative to quantum dots contained in any of the other quantum dot containing layer, wherein each quantum dot-containing layer is separated from other quantum dot containing layers by a spacer layer, and wherein a ratio of fluorescent intensities from the quantum dots in the plurality of quantum dot containing layers after simultaneous excitation defines a unique barcode for the microstructure. In various embodiments, the microstructure is between 10 nm and 5 mm in diameter; comprises at least two-three quantum dot-containing layers; has spacer layers that are between 10 nm and 100 nm in thickness; has the quantum dots covalently embedded in the quantum-dot containing layers; has a core comprising superparamagnetic material; comprises a spacer layer coated over the core; has the plurality of distinct layers comprise silica-containing layers; and/or further comprises one or more probes attached to an outer surface of the microstructure.

In a further aspect, the invention provides methods for molecular recognition comprising:
(a) contacting the molecular recognition system of the invention with a test sample under conditions suitable for binding of the one or more probes to a target if present in the test sample;
(b) removing unbound microstructures;
(c) detecting fluorescence from microstructures bound to the test sample; and
(d) identifying presence of one or more targets in the test sample based on a ratio of fluorescence intensity emissions from microstructures bound to the test sample.

In a still further aspect, the present invention provides microstructures comprising:
(a) a hollow core;
(b) a shell surrounding the hollow core;
(c) one or more layers surrounding the shell, wherein the one or more layers comprise:
(i) superparamagnetic material; and
(ii) photoluminescent materials.

In various further embodiments, the microstructure of this third aspect of the invention further comprises a therapeutic agent, diagnostic agent, contrast agent, and/or an imaging agent loaded into the hollow core.

In another aspect, the invention provides methods for making microstructures of the first or third aspect of the invention, comprising:
(a) providing a core;
(b) coating the core with a plurality of distinct layers, wherein each layer is applied sequentially, wherein the plurality of distinct layers comprises (i) quantum dot-containing layers, and (ii) spacer layers not containing quantum dots, wherein there are at least two quantum dot containing layers; wherein the quantum dots are present in each quantum dot containing layer at a defined intensity level, wherein each quantum dot containing layer comprises a single type of quantum dot that is different relative to quantum dots contained in any of the other quantum dot containing layers, wherein each quantum dot-containing layer is separated from other quantum dot containing layers by a spacer layer, and wherein a ratio of fluorescent intensities from the quantum dots in the plurality of quantum dot containing layers after simultaneous excitation defines a unique barcode for the microstructure.

In a further aspect, the invention provides methods for delivering a therapeutic agent, a diagnostic agent, a contrast agent, or an imaging agent to a subject in need thereof, comprising administering the microstructure of the first or third aspects of the invention, wherein the microstructure comprises a agent, a diagnostic agent, a contrast agent, or an imaging agent loaded into the hollow core.

BRIEF DESCRIPTION OF FIGURES

FIG. 3 (a) SEM and (b) TEM images of the as-prepared superparamagnetic, highly photoluminescent, hollow $SiO_2$ microstructures embedded with $Fe_3O_4$ nanoparticles and CdSe@ZnS QDs.

DESCRIPTION OF THE INVENTION

In a first aspect the present invention provides a microstructure comprising:

(a) a core; and
(b) a plurality of distinct layers surrounding the core; wherein the plurality of distinct layers comprises (i) quantum dot-containing layers, and (ii) spacer layers not containing quantum dots, wherein there are at least two quantum dot containing layers; wherein the quantum dots are present in each quantum dot containing layer at a defined intensity level, wherein each quantum dot containing layer comprises a single type of quantum dot that is different relative to quantum dots contained in any of the other quantum dot containing layer, wherein each quantum dot-containing layer is separated from other quantum dot containing layers by a spacer layer, and wherein a ratio of fluorescent intensities from the quantum dots in the plurality of quantum dot containing layers after simultaneous excitation defines a unique barcode for the microstructure.

The microstructures of the present invention provide the basis for generating a multiplex detection system based on the unique barcode associated with each microstructure. Thus, by providing a series of such microstructures, a powerful molecular recognition system is provided. Thus, in a second aspect, the present invention provides a molecular recognition system comprising a plurality of different populations of the microstructures of the first aspect, wherein each population has a unique bar-code based on the quantum dots present in the microstructure.

The microstructure specific emission spectra and intensity ratio can be rapidly identified providing an easily readable barcode for each individual microstructure. Aggregation of the quantum dots in different layers is minimized by use of the spacer layers, thereby reducing spectral interference and facilitating visibility. Aggregation of quantum dots within a given layer can be minimized or prevented through the covalent binding of the QDs within the layer (see, for example, references 15, 19, 28). The number of barcodes increases exponentially when multiple emission color and multiple intensities are used at the same time. When combined with probes attached to the microstructures, the molecular recognition system can be used, for example, in rapid multiplex detection methods. In various embodiments the microstructures can be used, for example, in array systems, flow cytometry systems, diagnostic libraries, combinatorial libraries, fluorescent inks, or fluorescent cosmetics.

As used herein, the "core" is the central portion of the microstructure and can be hollow, partially hollow, or solid. In various embodiments, hollow cores can be modified to include, for example, liquid, gas, particulate matter, or combinations thereof, as desired for a given application. When hollow, the cores can be loaded with, for example, therapeutic agents, diagnostic agents, contrast agents, and/or imaging agents, as described in more detail below. The core can be made of any material suitable for forming the microstructures of the invention, including inorganic materials, organic materials, polymeric materials, superparamagnetic materials (see below) or combinations thereof.

As used herein, a "quantum dot" (QD) is a semiconducting photoluminescent material, as is known in the art (For example, see Alivasatos, Science 271:933-937 (1996)). Non-limiting examples of QDs include: CdS quantum dots, CdSe quantum dots, CdSe@CdS core/shell quantum dots, CdSe@ZnS core/shell quantum dots, CdTe quantum dots, PbS quantum dots, and/or PbSe quantum dots. As is known to those of skill in the art, CdSe@ZnS means that a ZnS shell is coated on a CdSe core surface (ie: "core-shell" quantum dots). The shell materials of core-shell QDs have a higher bandgap and passivate the core QDs surfaces, resulting in higher quantum yield and higher stability and wider applications than core QDs.

Each quantum dot containing layer comprises a single type of quantum dot of a specific emission color. The "quantum dot containing layers" can be made of any material suitable for use with the microstructures that (a) allows excitation light to reach the quantum dots and allows fluorescence generated from the quantum dots to pass through the layers (ie: so it can be detected) and (b) can be combined with quantum dots to form a layer. Examples of materials that can be used to form layers containing quantum dots include, but are not limited to inorganic, organic, or polymeric material, each with or without biodegradable properties, and combinations thereof. In various embodiments, the layers can comprise silica-based compounds or polymers. Exemplary silica-based layers can include, but are not limited to, those comprising tetramethoxy silane or tetraethylorthosilicate. Exemplary polymer layers include, but are not limited to, those comprising polystyrene, poly (methyl methacrylate), polyhydroxyalkanoate, polylactide, or co-polymers thereof.

The "layers not containing quantum dots" (ie: spacer layers) serve as a barrier to prevent interactions between different QD layers, and can be made of any material suitable for use with the microstructures that (a) allows excitation light to reach the quantum dots in the quantum dot containing layer(s) below it in the microstructure and allows fluorescence generated from those quantum dots to pass through it (ie: so it can be detected) and (b) can segregate the quantum dots in one layer from those in other layers. Examples of materials that can be used to form spacer layers are the same as for the quantum dot containing layers.

The materials used for the quantum dot containing and spacer layers can be the same or different. In one embodiment, the same material is used in the quantum dot containing layers and the spacer layers.

The quantum dot containing layers and the spacer layers within a given microstructure can be any thickness suitable for use with microstructures and can be varied. For example thicker QD-containing layers allow for the loading of increased QDs in the shell, resulting in greater fluorescence intensity for that layer than for a thinner layer containing the same concentration of QDs. Thus, varying layer thickness can facilitate preparing QD-containing layer of various intensities. In various embodiments, the QD-containing layers can be between 5 nm and 500 nm; 10 nm and 500 nm; 5 nm and 100 nm, and 10 nm and 100 nm. Those of skill in the art will understand that other methods for varying intensity also exist, for example, modifying concentrations of the same QD in one microstructure with a first unique barcode compared to a second microstructure with a different fluorescent barcode. The ability to vary the intensities for the same QD color allows for an increased number of distinct and distinguishable microstructures (ie: more unique barcodes). In one embodiment, the spacer layers are greater than 10 nm, up to approximately 5 µm thick; in various other embodiments, the spacer layers are greater than 10 nm up to approximately 500 nm thick; in another embodiment greater than 10 nm up to approximately 100 nm thick.

The quantum dot-containing and spacer layers can be arranged in any order useful for a given application. Examples include, but are not-limited to, alternating QD-containing layers and spacer layers, or quantum dot containing layers separated by more than one spacer layer. Thus, a "spacer layer" can comprise a single layer, or may comprise two or more such spacer layers.

The microstructures of the present invention can comprise any number of quantum dot containing layers suitable for use with the microstructure. For example, the microstructures may comprise 2, 3, 4, 5, 6, 7, 8, 9, 10, or more quantum dot-containing layers and an appropriate number of spacer layers based on the number of quantum dot-containing layers. In various embodiments the number of quantum dot containing layers in a given microstructure can range from 1 to "m," where "m" is the number of quantum dots that can be used.

As used herein, "defined intensity level" refers to a known amount of quantum dots in each quantum dot containing layer, resulting in a known amount of fluorescent intensity generated from the QD containing layer upon appropriate stimulation. Since each QD containing layer has a defined intensity level, each microstructure will possess a defined ratio of fluorescence intensities generated from the various QD-containing layers upon stimulation. This defined ratio is referred to herein as a "barcode." Thus, each type of microstructure with the same QD layers possesses a similar barcode that can be distinguished from microstructures with different QD layers.

Thus, each quantum dot containing layer comprises a single type of quantum dot of a specific emission color and the layer is produced to posses a defined intensity level, based on the concentration of the QD in the layer. By varying the intensity levels of QDs ("n") in different microstructures and using a variety of different quantum dots ("m"), the number of different unique barcodes (and thus the number of different unique microstructure populations that can be produced) is approximated by the equation, $(n^m - 1)$ unique codes. This provides the ability to generate a very large number of different populations of microstructures each with its own unique barcode.

Table 1 provides a non-limiting illustration of how combinations of various QD-containing layers of defined intensity (referred to in the table simply by number for ease of illustration) and emission fluorescence (referred to herein as "color" for ease of reference) can produce 5 examples of different microstructures each with a unique bar-code.

TABLE 1

Examples of unique microstructures

| | Example | | | | |
|---|---|---|---|---|---|
| Layer # | 1<br>6 total layers | 2<br>5 total layers | 3<br>7 total layers | 4<br>3 total layers | 5<br>6 total layers |
| 1 | Non-QD | QD (green: 4) | Non-QD | QD (red: 6) | Non-QD |
| 2 | QD (green: 3) | Non-QD | QD (yellow: 2) | Non-QD | QD (green: 2) |
| 3 | Non-QD | QD (red: 5) | Non-QD | QD (green: 2) | Non-QD |
| 4 | QD (blue: 5) | Non-QD | QD (green: 7) | | QD (blue: 7) |
| 5 | Non-QD | QD (blue: 2) | Non-QD | | Non-QD |
| 6 | QD (yellow: 5) | | QD (red: 4) | | QD (green: 3) |
| 7 | | | Non-QD | | |
| Bar code | G3B5Y5 | G4R5B2 | Y2G7R4 | R6G2 | G2B7G3 |

Those of skill in the art will recognize, based on the teachings herein, the wide variety of such unique barcode microstructures that can be prepared according to the present invention.

The microstructure can be any diameter suitable for use in a given application. In one embodiment the microstructure has a diameter of 10 nm to 5 mm. In various other embodiments the diameter can range between 10 nm-2 mm, 10 nm-1 mm, 10 nm-500 µm, 25 nm-250 µm, 50 nm-2 mm, 50 nm-1 mm, 50 nm-500 nm, 50 nm-100 µm, 50 nm-10 µm, 100 nm-2 mm, 100 nm-1 mm, 100 nm-500 µm, 100 nm-100 µm, 100 nm-10 µm, 200 nm-2 mm, 0.200 nm to 1 mm, 300 nm-2 mm, and 300 nm-1 mm.

The microstructure may further comprise other components as desired for different applications, including but not limited to one or more coatings surrounding the microstructure. In one embodiment, an outer surface of the microstructure may be functionalized to provide binding sites for one or more compounds of interest, such as probes (see below). Such functionalization can include, but is not limited to, functionalizing the surface to contain reactive groups, such as hydroxyl, amine, carboxyl, thiol, or other groups that can be used to chemically link compounds of interest to the surface of the microparticle.

In a further embodiment, the microstructures further comprise one or more probes attached to an outer surface of the microstructure. Any number of probes can be attached by any method suitable for attaching the probe to the microstructure. Any type of probe that is useful for a desired purpose can be used, including but not limited to detecting a target of interest that the probe binds to. The probes attached to a given microstructure can all be the same or can be varied. Examples of suitable probes include, but are not limited to, nucleic acids, proteins, antibodies, polysaccharides, lipids, organic molecules, or inorganic molecules. Such probe-containing microstructures and molecular recognition systems are particularly useful for multiplex analysis of targets of interest in a variety of solid-phase assay formats, including but not limited to immunocytochemistry, ELISAs, EIAs, dipstick-based assays, Western blot analysis, microarray analysis of any type (DNA, RNA, protein, carbohydrate, etc.), and high throughput diagnostic arrays for determining, for example, species of viral or bacterial infection, types of malignancies, or genetic mutations.

In various embodiments of the invention, the microstructures of the invention further comprise a superparamagnetic material. In one embodiment, the core comprises a superparamagnetic material, such as a superparamagnetic nanoparticle. In another embodiment, one or more layers (QD containing, non-QD containing, or both) comprises a superparamagnetic material; in this embodiment, the core may or may not also comprise a superparamagnetic material. As used herein "superparamagnetic" is defined as exhibiting magnetic properties in a magnetic field with no residual magnetism once the field is removed. Examples of superparamagnetic compositions include, but are not limited to, $Fe_3O_4$ nanoparticles, $Fe_2O_3$ nanoparticles; Mg/Co/Mn doped iron oxide nanoparticles, and FePt nanoparticles or combinations thereof.

In a further aspect of the invention, methods for making microstructures are provided, comprising:

(a) providing a core;
(b) coating the core with a plurality of distinct layers, wherein each layer is applied sequentially, wherein the plurality of distinct layers comprises (i) quantum dot-containing layers, and (ii) spacer layers not containing quantum dots, wherein there are at least two quantum dot containing layers; wherein the quantum dots are present in each quantum dot containing layer at a defined intensity level, wherein each quantum dot containing layer comprises a different type of quantum dot relative to any the other quantum dot containing layer, wherein each quantum dot-containing layer is separated from other quantum dot containing layers by a spacer layer, and wherein a ratio of fluorescent intensities from the quantum dots in the plurality of quantum dot containing layers after simultaneous excitation defines a unique barcode for the microstructure.

Thus, the methods comprise methods for making the microstructures of the first aspect of the invention, as well as the fifth aspect of the invention (see below). The microparticles of the invention can be made by any suitable technique, including but not limited to the methods disclosed herein. In general, the methods comprise forming a plurality of layers around a core, wherein the layers are as described above for the microstructures of the invention. In one embodiment the method further comprises embedding the quantum dots covalently in the quantum-dot containing layers. (See, for example, references 15, 19, and 28). In one non-limiting embodiment, the quantum dots are "capped" with an agent to facilitate covalent binding to the layers. Capping agents can include, but are not limited to any thiol-modified ligands, including MPS, mercaptopropyl acid, and thiol-modified DNA.

In one embodiment, a sol-gel method is used to produce a template or layers, when the template or layers are made of silica. As used herein "sol-gel method" means a colloidal suspension that can be gelled to form a solid and is well known to those skilled in the art. Non-limiting exemplary silica layers are derived from alkoxysilane, such as tetramethoxy silane, tetraethylorthosilicate, sodium silicate or combinations thereof.

As used herein "template" means any solid core material that can support the addition of layers surrounding it. In certain embodiments where a hollow core is desired, the template must be one that can be removed after the addition of layers. The template can be any desired shape, but is generally substantially spherical. The template can be a permanent part of the microstructure (ie: the core) or it can be removed during production of the microstructure (to create hollow microparticles). The template can be made of any material suitable including, but not limited to, inorganic materials, organic materials, polymeric materials, superparamagnetic materials, or combinations thereof. In various embodiments the template can be made from polystyrene, poly(methyl methacrylate), polyhydroxyalkanoate, polylactide, or combinations thereof. Removal of the template, if desired, can be accomplished by any procedure suitable for removal including, but not limited to, dissolution or calcination.

In another embodiment, a polymerization method is used to produce the template or layers, when the template or layers are made of a polymer. Non-limiting, exemplary polymer layers include polystyrene, poly(methyl methacrylate), polyhydroxyalkanoate, polylactide, or combinations thereof. The methods for forming the layers are basically the same using sol-gel or polymerization techniques, except for the choice of layer material.

In specific, non-limiting embodiments the microstructure is in solution during its preparation, to produce a liquid template core, or is dried, resulting in a template core in a gaseous state.

The methods for making the microstructures of the present invention result in minimal aggregation of the quantum dots in the microstructure, due to the use of spacer layers between the QD-containing layers and covalent binding with the matrix to ensure that the QDs are well dispersed in the matrix. In one embodiment, covalent binding of the QD to the matrix comprises adding a ligand (also referred to herein as a capping agent). This provides a distinct advantage over previous methods for making quantum dot-containing particles, and allows for precise control of quantum dot placement and quantity in each QD-containing layer, since the quantities of the QDs loaded in each layer are precisely controllable, as well as the fluorescence intensity ratio of QDs placed in different layers.

In a further aspect the present invention provides a method for molecular recognition comprising:

(a) contacting a molecular recognition system as disclosed above with a test sample under conditions suitable for binding of the one or more probes to a target if present in the test sample;
(b) removing unbound microstructures;
(c) detecting fluorescence from microstructures bound to the test sample; and
(d) identifying presence of one or more targets in the test sample based on a ratio of fluorescence intensity emissions from microstructures bound to the test sample.

The methods of this aspect of the invention utilize the microstructures (and molecular recognition system) of the invention, as disclosed above, and are particularly useful for multiplex analysis of targets of interest in a variety of solid-phase assay formats, including but not limited to immunocytochemistry, ELISAs, EIAs, dipstick-based assays, Western blot analysis, microarray analysis of any type (DNA, RNA, protein, carbohydrate, etc.), and high throughput diagnostic arrays for determining, for example, species of viral or bacterial infection, types of malignancies, or genetic mutations. In one non-limiting illustration, two different populations of microstructures are provided:

(1) Population 1 comprising Probe A that binds to Target A, and where the microstructures in the population all have a unique barcode of R1G2B3; and
(2) Population 2 comprising Probe B that binds to Target B, and where the microstructures in the population all have a unique barcode of R5G1B8.

These two populations of microstructures (forming a molecular recognition system) are contacted to a test sample, preferably a solid phase system under conditions promoting binding of Target A to Probe A and Target B to Probe B, if Target A and Target B are present in the test sample. After binding, unbound probe (ie: unbound microstructures) are removed via any suitable technique (including but not limited to a wash step or by magnetic means), and the test sample is subjected to excitation by an appropriate wavelength(s) of light. The resulting fluorescence emission spectrum from the bound microstructures is then detected via any suitable technique (including but not limited to fluorescence spectroscopy, a fluorescence barcode reader, and laser scanning confocal microscopy), and a ratio of fluorescence intensity emissions from microstructures bound to the test sample are determined, which correlates with the presence of Target A or B in the test sample (ie: R1G2B3 correlates with the presence of Target A and R5G1B8 correlates with the presence of Target B).

In a further non-limiting example, four different antibody probes are attached to four different populations of microstructures that each emits a unique fluorescence intensity ratio based on emission color and intensity of the quantum dots. These would then be used for immunocytochemistry, by methods known to those with skill in the art, to assay for the presence of four different antigens in the same test sample tissue. The unbound antibody-attached-microstructures are washed off of the sample tissue so that detection of the unique bar-code emission spectra intensity ratio for each antibody-attached-microstructure would signal the presence of the antigen of interest in the test sample tissue. This would allow for quadruple labeling of the test sample tissue with minimal incubation washes and visualization of all label results simultaneously.

Example 2 below provides a specific example of using the microstructures of the present invention in 2D Western blotting.

Those of skill in the art will clearly understand, based on the teachings herein, that the methods can involve any number of different particles and thus be used for large multiplex analysis and a wide variety of assay formats.

In a fourth aspect the present invention provides a microstructure, comprising:
(a) a hollow core;
(b) a shell surrounding the hollow core;
(c) one or more layers surrounding the shell, wherein the one or more layers comprise:
(i) superparamagnetic material; and
(ii) photoluminescent materials.

In various embodiments the hollow core can be loaded with liquid (such as pharmaceuticals, diagnostics, contrast agents, or dyes) or gas agents (such as pharmaceutical or contrast-enhancement agents).

The hollow core can be loaded or filled by any method suitable for loading a liquid or gas. In a non-limiting embodiment, if it is desired that the core contain a drug, the microstructures may, for example, be soaked in a solution of the drug whereby the solution diffuses into the hollow core.

In various embodiments the hollow core can be filled with a therapeutic agent. Examples of such agents include, but are not limited to agents for the common cold, anti-addiction, anti-infectives, analgesics, anesthetics, anorexics, anti-arthritics, anti-allergy agents, anti-asthmatic agents, anticonvulsants, anti-depressants, anti-diabetic agents, anti-depressants, anti-diuretics, anti-emetics, antihistamines, anti-inflammatory agents, anti-migraine preparations, anti-motion sickness preparations, anti-nauseants, anti-neoplastics, anti-obesity, anti-osteoporeteic, anti-Parkinsonism drugs, anti-pruritics, anti-psychotics, antipyretics, anti-cholinergics, benzodiazepine antagonists, bone stimulating agents, central nervous system stimulants, hormones, hypnotics, immunosuppressives, prostaglandins, proteins, peptides, polypeptides and other macromolecules, psychostimulants, rhinitis treatment, sedatives, sexual hypofunction treatments, tranquilizers and vitamins including B12, enzymes, steroids, genetic material, viral vectors, antisense agents, proteins, peptides, anti-tumor agents and combinations thereof. Examples of specific drugs or therapeutic agents include, but are not limited to, butorphanol, calcitonin and analogs, COX-II inhibitors, desmopressin and analogs, dihydroergotamine, dopamine agonists and antagonists, enkephalins and other opioid peptides, growth hormone and analogs (including growth hormone releasing hormone), growth hormone antagonists, IgE suppressors, insulin, insulinotropin and analogs, ketamine, kytril, leutenizing hormone releasing hormone and analogs, lidocaine, metoclopramide, midazolam, narcotic analgesics, neuraminidase inhibitors, nicotine, non-steroidal anti-inflammatory agents, oligosaccharides, ondansetron, parathyroid hormone and analogs, parathyroid hormone antagonists, prostaglandin antagonists, prostaglandins, recombinant soluble receptors, scopolamine, serotonin agonists and antagonists, sildenafil, terbutaline, vasopressin. In further non-limiting examples, the hollow core could be filled with vaccines with or without carriers/adjuvants such as prophylactics and therapeutic antigens (including but not limited to subunit protein, peptide and polysaccharide, polysaccharide conjugates, toxoids, genetic based vaccines, live attenuated, reassortant, inactivated, whole cells, viral and bacterial vectors) in connection with, arthritis, cholera, cocaine addiction, HIB, meningococcus, measles, mumps, rubella, varicella, yellow fever, respiratory syncytial virus, pneumococcus, *streptococcus*, typhoid, influenza, hepatitis, including hepatitis A, B, C and E, polio, HIV, parainfluenza, rotavirus, CMV, chlamydia, non-typeable *haemophilus, moraxella catarrhalis*, human papilloma virus, tuberculosis including BCG, gonorrhoea, asthma, atheroschlerosis, malaria, otitis media, *E-coli*, Alzheimer's, *H. Pylori, salmonella*, diabetes, cancer and herpes simplex.

In various other embodiments the hollow core can be filled with a diagnostic, contrast, or imaging agent. Examples of such agents include, but are limited to radionuclides, contrast media, ferromagnetic materials such as iron oxide, perfluorochemicals such as perfluorooctylbromide, or gamma emitting radiolabels such as Technetium-99m, Indium-111, Gallium-67, Thallium-201, Iodine-131, 125, or 123, positron emitting radiolabels such as Fluorine-18, or those produced by neutron activation such as Samarium-153, other radioactive isotopes and radio-opaque agents (barium, bromine and phosphorus-containing compounds), radiolucent agents, dyes (e.g., fluorescent dyes and chromophores), gasses, and enzymes that catalyze a calorimetric or fluorometric reaction, or combinations thereof.

In embodiments where a "templating" is used to generate the hollow core, the "shell" comprises a coating placed on a template for the core which remains after dissolution or calcination of the core template material. In embodiments, where a non-templating method is used to generate the hollow cores, the shell may comprise a layer. Any suitable shell can be used, including but not limited to silica, liposome, chitosan, polymers, or combinations thereof.

Templates are as disclosed above. Removal of the template can be accomplished by any procedure suitable for removal including, but not limited to, dissolution or calcination. Any number of layers as desired for a given application can be placed over the core and shell.

As used herein "photoluminescent materials" can be any suitable photoluminescent material, but preferably are quantum dots, as described above. Such QDs include, but are not limited to, CdS quantum dots, and/or CdSe quantum dots, and/or CdSe@ZnS core/shell quantum dots, and/or CdTe quantum dots, and/or PbS quantum dots, and/or PbSe quantum dots, and/or organic fluorophore. The layers can comprise QD-containing layers, non-QD containing layers (spacer layers), or any combination thereof. Embodiments of QD-containing and non-QD-containing layers and microstructures including both are as disclosed above. The microstructures of this aspect can also comprise unique barcodes as discussed above.

Superparamagnetic materials and embodiments thereof are as described above. In various embodiments, the superparamagnetic materials can be in the same layer as the photoluminescent materials or in different layers; more than one type of superparamagnetic material can be used in a given microstructure whether in the same layer or not; and the shell may also comprise superparamagnetic materials, for example, when the shell is itself a layer.

In various embodiments the core size and shell thickness can be varied and can be any size or thickness suitable for the microstructures. Embodiments of the core are as disclosed above.

The microstructures of this fifth aspect of the invention can be made by any suitable method, including those disclosed herein.

The microstructures of the fifth aspect of the invention can be used for delivery of drugs, diagnostic agents, imaging agents, contrast agents, etc., to a subject in need thereof. In one non-limiting embodiment, the microstructure can be used to target the hollow structure as a drug carrier to a specific site by using an external magnet and to monitor the drug delivery behavior by visualizing the fluorescent quantum dots encapsulated in the microstructure layers.

In a non-limiting example the microstructure of this aspect could be useful for targeting an anti-tumor drug to the specific part of the body where the tumor is located. This would prevent the whole body from being exposed to the agent and would also allow visualization of the tumor targeted by the agent.

Thus, in a further aspect, the present invention provides methods for administration of a therapeutic agent, diagnostic agent, imaging agent, and/or contrast agent, comprising administering to the subject in need thereof a microstructure of the fifth aspect of the invention wherein the microstructure comprises one or more therapeutic agent, diagnostic agent, imaging agent, and/or contrast agent, in the hollow core. One of skill in the art, such as a physician, can determine an appropriate amount of agent to administer to a given subject.

In a further embodiment, the method comprises targeting the microstructure to a specific location in the subject by using an external magnet and/or monitoring location of the microstructure in the subject by detecting photoluminescence from the microstructure in the subject. (See, for example, Salabas and Schüth F 2007 Magnetic Nanoparticles Synthesis, Protection, Functionalization, and Application *Angew. Chem. Int. Ed.* 46 1222-44; Gao, et al, "*Nature Biotechnology* 2004, 22, 969-976).

Example 1

Superparamagnetic, Fluorescent Barcode Microstructures

Figure 1:
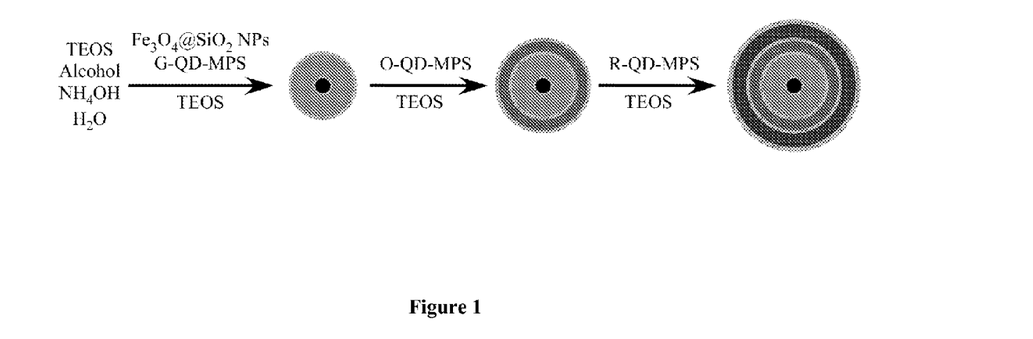
FIG. 1 is a non-limiting illustration of the microstructure fabrication scheme.

FIG. 1 illustrates one strategy for the layer-by-layer synthesis of the barcode microstructures through combination of QD surface chemistry and sol-gel chemistry, which is based on the inorganic-organic hybrid approach by introducing mercaptopropyl trimethoxysilane (MPS)-capped QDs into silica network through sol-gel chemistry [27, 28]. (ie: capped to help reduce/prevent aggregation within layers). Capping agents can include, but are not limited to any thiol-modified ligands, including MPS, mercaptopropyl acid, and thiol-modified DNA. The MPS-capped CdSe@ZnS-containing microstructures were prepared in two steps based on the original low temperature synthetic method reported by us [28-31]. First, the silica coated $Fe_3O_4$ NPs serve as core, and the MPS-capped QDs co-condense with tetraethyl orthosilicate (TEOS) to form the first layer of QD-silica network. Secondly, a spacer layer of pure silica deposits on the outside surface of the first layer. The growth of further QDs-containing layer and spacer layer is repeated by addition of different colored MPS-capped QDs and TEOS, consecutively.

Our preferred strategy offers the following unique features: 1) the location of the magnetic NPs and the QDs in the silica spheres are separated spatially so that no interference of the QD PL by the magnetic particles is expected [19, 23]; 2) the photoluminescence spectrum (PL spectra) of barcode microstructures can be easily tuned through varying the ratio of different QDs loaded in the different layers; 3) the size of the silica microstructures can range from submicron to micrometers depending on the number of layers and the thickness of each layer; 4) QDs' chemical and photo-stability is preserved by embedding the QDs covalently in the silica matrix [15, 19, 28]; 5) FRET between different colored QDs are avoided by isolating them into separated layers with a silica spacer layer (>10 nm). [14, 32].

Experimental Details

Preparation of MPS-Capped CdSe@ZnS Core/Shell QDs

First, oleylamine-capped CdSe QDs with green, yellow, and red emission colors were obtained using our established method [30, 31]. In a typical synthetic process, 0.2 mmol $B_2Se_3$ and 0.6 mmol $CdCl_2$ was loaded separately into 3 mL oleylamine in sealed vials and dissolved by heating at 110° C. for 20 minutes. After the solutions were cooled down to room temperature, they were mixed together and divided into three 15-mL crimp-top vials. Each mixture solution was heated at 75, 140 or 260° C. for 1 hour in a convectional oven. The reactions at different reaction temperatures yielded products with different PL emission wavelengths ($\lambda_{max}$=533, 584 and 634 nm, respectively).

The CdSe@ZnS QDs with MPS as the capping ligand were prepared using our recently published method [28, 29], achieving coating the CdSe QDs with a ZnS coating, and replacing oleylamine (the original capping ligand) by MPS simultaneously. This method avoids any possible decrease of quantum yield (QY) during the ligand exchange process [29]. In a typical reaction, 0.1 mmol $P_2S_5$, 1.2 g MPS and 0.5 mL butylamine were heated at 110° C. for 20 minutes in 10 mL 1-methyl-2-pyrrolidinone (NMP) in a sealed vial to dissolve the sulfide. In a separate vial, 0.5 mmol $ZnCl_2$, 1.2 g MPS and 0.5 mL butylamine were mixed in 10 mL NMP and heated to dissolve in the same way. After cooling down to room temperature, the $ZnCl_2$ solution was divided into five crimp-top vials. 0.01 g of oleylamine-capped CdSe particles were dissolved in the $P_2S_5$ solution and the whole solution was divided into five portions. Each portion of the CdSe/$P_2S_5$ solution was injected into one $ZnCl_2$ solution preheated at 70° C. and the mixture solution was kept at the same temperature for 1 hour in a convectional oven, which yielded the MPS-capped CdSe@ZnS QDs. The CdSe@ZnS QDs were concentrated by solvent extraction 3 to 5 times using hexane, and redispersed in 10 mL isopropanol. The QYs of the as-prepared green-, yellow-, and red-emission QDs are 72.3%, 25.4%, and 26.3%, respectively.

Preparation of Thin Silica Layer Coated $Fe_3O_4$NPs

Monodisperse $Fe_3O_4$ NPs (diameter 10±2 nm) were prepared according to reference 33. The thin, dense silica coating on $Fe_3O_4$NPs is achieved by hydrolysis of sodium silicate in a basic solution and condensation on the surfaces of the $Fe_3O_4$ NPs. In a typical reaction, 1 g $Fe_3O_4$NPs were dispersed in 100 mL deionized water by 30 minutes ultrasonication. The suspension was then mechanically stirred under nitrogen flowing for 12 hours at 60° C. 10 mL of 1 mol/L sodium silicate solution was drop wise added to the suspension, which initiated the hydrolysis and condensation of silicate on the $Fe_3O_4$ NP surfaces. The pH of the solution was maintained at 10 by adding aliquots of 0.5 mol/L HCl solution. The silica coated $Fe_3O_4$ NPs were thoroughly washed with deionized water five times and collected using a magnet. The magnetic NPs contained a thin, dense layer of silica (~5 nm) that sealed the $Fe_3O_4$ NPs surfaces.

Preparation of Superparamagnetic, Fluorescent Barcode Microstructures Through Lay-by-Layer Growth Method In a typical reaction, 0.02 g silica coated $Fe_3O_4$ NPs aqueous solution were dispersed in a mixture solution of 50 mL isopropanol, 5 mL water and 2 mL ammonia solution (28-30%) in a 200 mL three-neck flask with mechanical stirring and nitrogen flow. 1 mL of MPS-capped CdSe@ZnS QDs (green emission) isopropanol solution was drop wise added into the above solution. 0.5 hour later, 0.2 mL of tetraethoxysilane (TEOS) was slowly added, and was co-condensed with MPS-capped QDs onto the silica coated $Fe_3O_4$NPs surface. Three hours later, another 0.15 mL of TEOS was added to form a further silica spacer layer. The as-prepared product was purified with an external magnet and redispersed in the same composition of isoproponal/water solution for continuous reaction. By repeated addition of different emission color QDs (yellow and red) and TEOS, the multicolor QDs encoded silica microstructures were obtained, with $Fe_3O_4$ NPs in the core, and different QDs isolated and embedded in different layer of the silica layers. The size of the barcode microstructures and the PL intensity ratio of the different QDs in each unique barcoded microstructure can be conveniently tuned by changing the amounts of TEOS, MPS-capped QDs, ammonia concentration, or reaction time in each layer growth step.

FRET Control Experiment.

Two different microstructures containing green- and yellow-emission QDs were prepared by using layer-by-layer growth method and one-step sol-gel method. The layer-by-layer growth method is as described above. And the green-emission QDs were isolated from yellow-emission QDs with a $SiO_2$ spacer layer. In one-step sol-gel method, MPS-capped green QDs and yellow QDs were mixed together and added into the reaction, thus the two different QDs were randomly dispersed in $SiO_2$ micro structures.

Results and Discussions

As a demonstration, we synthesized three-layered barcode microstructures embedded with green-emission QDs ($\lambda_{max}$=534 nm) in the first layer, yellow-emission QDs ($\lambda_{max}$=585 nm) in the second layer and red-emission QDs ($\lambda_{max}$=634 nm) in the third layer. Aliquots of the reaction products were taken after each steps of layer-by-layer growth and characterized by fluorescence spectroscopy, scanning electronic microscopy (SEM) and laser scanning confocal microscopy.

The PL spectra of the microstructures after each step of growth were determined. After controlled growth of each layer encapsulating one type of QDs, the green-, yellow-, and red-emission peaks consecutively show up in the spectra, revealing the layer-by-layer growth mechanism of the microstructures. Comparing the PL spectra of the microstructures (suspended in water) with the individual QDs in isopropanol solutions, the PL emission peaks match well with negligible shifts. This suggests that the QDs maintain the same optical characteristics before and after the synthesis process and are evenly distributed within the silica matrix of each layer with negligible aggregation between the same colored QDs [15, 28]. Note that the asymmetric background in the PL spectra of the QD-embedded microstructures is due to the light scattering from the silica microstructures.

The samples were placed on a UV transluminator with 365 nm excitation that comes from the bottom of the vials. With only green QDs, the microstructure gave a green emission color. With the second layer of yellow QDs, the microstructure gives yellow-greenish emission color, which is the mixture color from green and yellow QDs. After the growth of red QDs in the third layer, the emission color becomes peach-orange, which is the mixture color of green, yellow and red. Using an external magnet, it is observed that the microstructures were all attracted to the side of the magnet, leaving the solution transparent. The faint blue color in the vials comes from the scattered UV incident light by the glass wall, but not from PL of any QDs. This observation illustrated that the QDs consecutively added during the preparation were all layer-by-layer grown onto the magnetic NP core as designed in FIG. 1.

The layer-by-layer growth was further monitored by SEM as the size increase of the silica microstructures after the growth of each QD layer. The SEM images indicate that the average diameters of the microstructures increase from 155 nm, to 270 nm and then to 330 nm. It is calculated that the volume of the second layer and third layer are the same with the same amount of reagents added. This result indicates that the growth of the silica layers is quantitative, and that the size of the microstructures and the thickness of each layer can be controlled precisely by adjusting the amount of the reaction regents in each step of the reaction. By controlling the feeding of MPS-QDs and TEOS (ie: control the reaction process and avoid the side-product of the reaction as described below), homogenous nucleation of MPS-QDs and/or TEOS was avoided in each growing step, indicated by the highly monodispersed silica microstructures and the transparency and lack of PL from the supernatant of the samples in the magnet field.

Laser scanning confocal microscopy (ZEISS, LSM 5 DUO) imaging of the microstructures in a single particle level was also used to confirm the concentric growth mechanism. The microstructures were spread on a glass slide and imaged with excitation wavelength at 405 nm. The confocal microscopy imaging only shows bright points in a dark background, and the colors were arbitrarily assigned. The superimposed images of the three samples clearly showed that the barcode microstructures were all well dispersed and uniformly colored, which manifested that the barcoding power keeps accurate on the individual small microstructures. The fact that the colors of microstructures in the superimposed images that are all the same within each image supports our proposed layer-by-layer grown mechanism: the latter QD layer was consecutively grown outside of the prior microstructures, which act as heterogeneous nucleation seeds for the co-condensation of MPS-QD and TEOS. Otherwise, different colored microstructures would be expected if some homogeneous nucleation occurs.

The barcoding capability of our microstructures can be achieved efficiently using a combinatorial layer-by-layer synthesis strategy. For quantitative spectral measurements (intensity vs. wavelength), confocal microscopy is less reliable than spectrofluorometry mainly due to the small size of the obtained microstructures and low intensities from individual particles, so spectrofluorometry was used to reveal the barcoding capability of our barcode microstructures. Various ratios of the green-, yellow-, and red-emission QDs barcode microstructures were achieved through our layer-by-layer strategy, clearly demonstrates the strategy's programmability. The PL intensity ratio of the barcode microstructures is determined by both the amount of QDs loaded and the quantum yields of the different QDs. The number of possible fluorescent barcodes that can be generated is only limited by the number of spectrally distinguishable QDs and the number of the PL intensity levels. The PL intensity ratio of the barcode microstructures is determined by both the amount of QDs loaded and the quantum yields of the different QDs, provided all the added MPS-capped QDs were co-condensed with TEOS to form the silica barcode microstructures. Since the quantum yields of the QDs were known in this work, the relative PL intensities ratio can then be tuned by varying the amounts of QDs.

In this example, the $Fe_3O_4$ NPs are encapsulated within a thin silica coating, which facilitates the co-condensation of MPS-QDs and TEOS onto the $Fe_3O_4$ NPs surface [34], and also avoids decrease of the PL intensity due to direct surface contact of the magnetic NPs with QDs [19, 23].

It was known that FRET can happen between fluorophores with a spectral overlap of the donor's emission and acceptor's absorbance when they are in close spatial proximity. Different from the barcode systems reported before [2, 6, 23, 35, 36], the synthesis strategy of our barcode microstructures separates the neighboring QDs containing layers with an inert spacer layer. In this example, it is estimated from the SEM size analysis that the two silica spacer layers between neighboring QDs containing-layers are greater than 10 nm, which is larger than the distance required for FRET to occur. Thus, FRET between QDs in the neighboring layers can be efficiently avoided, leading to more accurate barcoding. This important feature is confirmed by the FRET control experiment.

Comparing the emission spectra of the resulted two kinds of microstructures with those of the individual QDs, it was demonstrated that the sample prepared by the layer-by-layer method keeps the similar PL intensities as those of the individual QDs before the reaction, indicating negligible FRET happened between the QDs. On the other hand, a concomitant intensity decrease of the green-emission QDs and an intensity increase of the yellow-emission QDs for the product from the one-step reaction, which indicates that FRET occurs. It was also noted that the relative PL intensities of the QDs in the $SiO_2$ microstructures did not change with following growth of QDs. This again indicates that FRET does not happen between the QDs that are spatially separated in different layers.

The lifetime measurements of the green-emission in the as-prepared two barcode microstructures provided an independent proof of the energy transfer from green-emission QDs to yellow-emission QDs. The PL intensities were normalized for direct comparing their time dependence. The green-emission QDs in the sample prepared by one-step method had a ~20% faster decay than that of the sample prepared by layer-by-layer method. This result indicated the FRET happened between the green QDs and yellow QDs in the samples obtained from one-step method with FRET efficiency of ~20%, which is consistent with the FRET efficiency calculated from spectral measurements.

Conclusions

In summary, we described a new strategy to synthesize multi-component barcode microstructures. This novel barcode microstructures provides high barcoding accuracy because FRET between different QDs is deliberately avoided with an isolated spacer layer, and it can be easily manipulated with an external magnet. Its barcoding capability can be easily tuned through ratioing of different QDs loaded in each layer. The QDs are covalently encapsulated in the silica network, therefore higher chemical stability and photo-stability are expected. We expect that this method could be easily adapted for both in vivo and/or in vitro biological imaging and molecular profiling.

Example 2

2D Western Blotting

The microstructures can be used in 2D western blot protein detection. Compared to conventional western blot protein detection, this new technology is multiplexing, more sensitive, higher stability and higher throughput. Compared to conventional 96 well plate based enzyme-linked immunosorbent assay (ELISA), this new technology is more economical with small protein samples and fewer antibodies. Crude proteins are obtained through cell lysis. Two dimensional gel electrophoresis is used to separate proteins, and the proteins are then transferred out of the gel onto a membrane (including but not limited to nitrocellulose). Microstructures (functionalized to bind to antibodies) with specific antibody to different proteins are prepared. The microstructures are immobilized to certain protein on the membrane based on the specific interaction between the antibody on the microstructure surface and the protein antigen. Excited by a UV light, different proteins are rapidly and precisely detected by different optical signals from the microstructure.

Example 3

Hollow Superparamagnetic, Photoluminescent Structures

Figure 2:
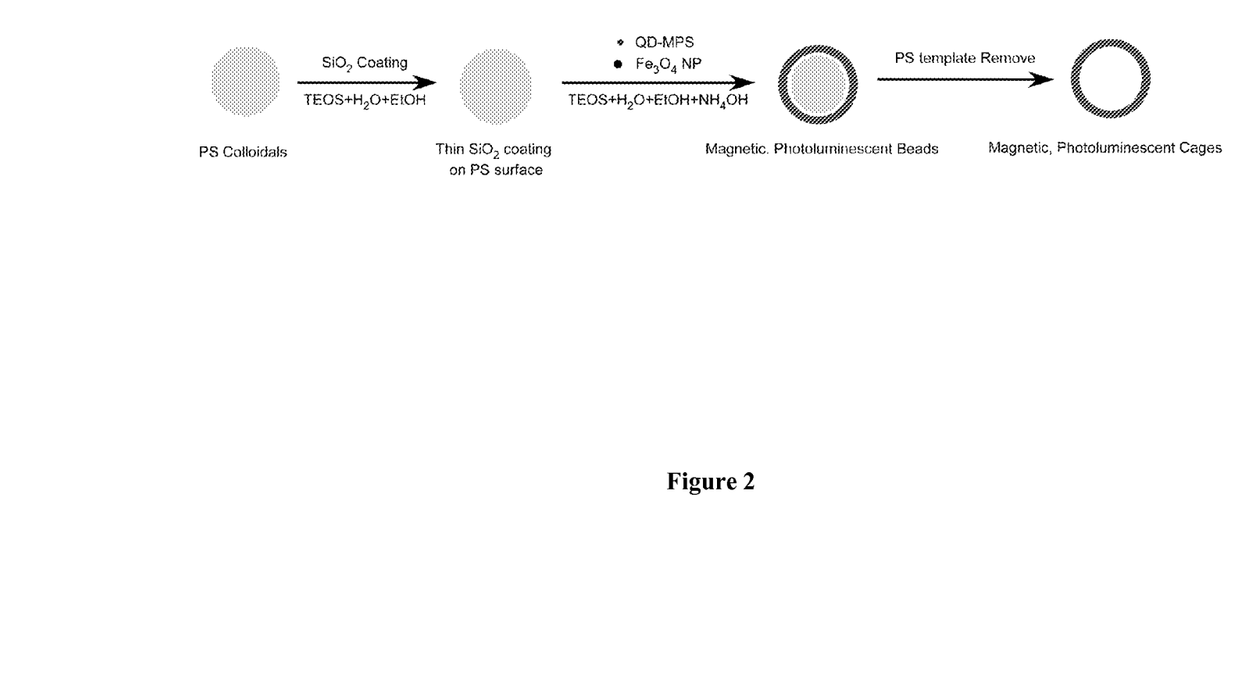
FIG. 2 illustrates one embodiment of the present invention of the process to prepare the hollow microstructure with superparamagnetic, highly photoluminescent properties.

FIG. 2 illustrates one embodiment of the present invention of the process to prepare the hollow microstructure with superparamagnetic, highly photoluminescent properties. In the first step, a thin layer a $SiO_2$ was deposited on a polystyrene (PS) template microsphere surface. The PS template is used here for the purpose of forming the template; in the last step it is dissolved or calcined, which ensures drug (if desired) can be loaded in the hollow core that is left. The conditions for the $SiO_2$ thin layer coating on the PS surface were as follows: 1 g of PS microspheres was dispersed in 30-100 g of alcohol solution with 5% to 25% (v/v) of $H_2O$. With stirring and $N_2$ flow, acid solution was added to adjust the solution pH to 2-3. Next, the silica precursor solution was added and the $SiO_2$ coated polystyrene microsphere was achieved. The prepared $SiO_2$ coated polymer microspheres were purified and dispersed in alcohol solution for the next step-wise reactions.

In the second step, fluorescent quantum dots and superparamagnetic materials were added in the above alcohol solution dispersed with $SiO_2$ coated polymer microspheres, followed by 5-25% (v/v) of $H_2O$, and base solution to get the pH of the mixture to 9-11. After that, a silica precursor was added into the mixture solution. The reaction was carried out under stirring and $N_2$ flow, and the superparamagnetic, highly photoluminescent $SiO_2$/polymer composite microspheres were achieved. The fluorescent material used here was CdSe@ZnS core/shell quantum dots. The superparamagnetic materials used here was $Fe_3O_4$ nanoparticles. Layers were added according the protocol detailed in Examples 1 and 2.

Figure 3A:
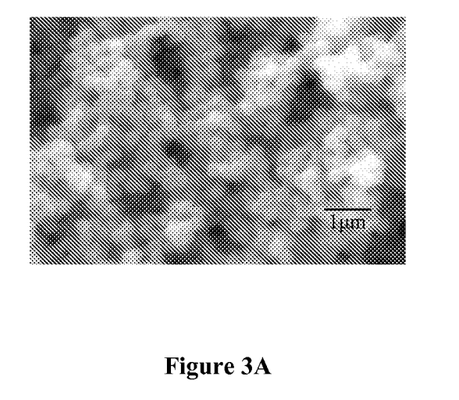
Figure 3B:
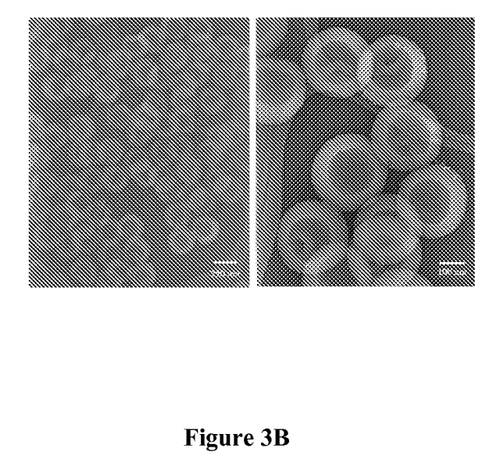

In the third step, the superparamagnetic, highly photoluminescent, hollow microstructure was achieved by dissolution of the polymer template microsphere. The solvent used to dissolve the polymer template microsphere was toluene. FIG. 3 shows the scanning electron microscopy (SEM) (3A) and transmission electron microscopy (TEM) (3B) images of as-prepared superparamagnetic, highly photoluminescent $SiO_2$ microstructures. The photoluminescence of the as-prepared hollow $SiO_2$ microstructures was detected.

The backgrounds of the emission curve are from the light scattering of as-prepared microstructures, but the different emission peaks from the as-prepared hollow $SiO_2$ microstructures embedded with different emission quantum dots can still be visualized.

REFERENCES CITED

[1] Nicewarner-Pena S R, Freeman R G, Reiss B D, He L, Pen D J, Walton I D, Cromer R, Keating C D and Natan M J 2001 Submicrometer metallic barcodes *Science* 294 137-41.
[2] Han M, Gao X, Su J Z and Nie S 2001 Quantum-dot-tagged microbeads for multiplexed optical coding of biomolecules *Nat. Biotechnol.* 19 631-5.
[3] Hill H D and Mirkin C A 2006 The bio-barcode assay for the detection of protein and nucleic acid targets using DTT-induced ligand exchange *Nat. Protocols* 1 324-36.
[4] Pierce S E, Fung E L, Jaramillo D F, Chu A M, Davis R W, Nislow C and Giaever G 2006 A unique and universal molecular barcode array *Nat. Methods* 3 601-3.
[5] Kuang M, Wang D, Bao H, Gao M, Moehwald H and Jiang M 2005 Fabrication of multicolor-encoded microspheres by tagging semiconductor nanocrystals to hydrogel spheres *Adv. Mater.* 17 267-70.
[6] Xu H, Sha M Y, Wong E Y, Uphoff J, Xu Y, Treadway J A, Truong A, O'Brien E, Asquith S, Stubbins M, Spurr N K, Lai E H and Mahoney W 2003 Multiplexed SNP genotyping using the Qbead™ system: a quantum dot-encoded microsphere-based assay *Nucleic Acids Res.* 31 (8) e43.
[7] Li Y, Cu Yen T H and Luo D 2005 Multiplexed detection of pathogen DNA with DNA-based fluorescence nanobarcodes *Nat. Biotechnol.* 23 885-9.
[8] Medintz I L, Uyeda H T, Goldman E R and Mattoussi H 2005 Quantum dot bioconjugates for imaging, labeling and sensing *Nat. Mater.* 4 435-46.
[9] Mornet S, Vasseur S, Grasset F and Duguet E 2004 Magnetic nanoparticle design for medical diagnosis and therapy *J. Mater. Chem.* 14 2161-75
[10] Kettering M, Winter J, Zeisberger M, Bremer-Streck S, Oehring H, Bergemann C, Alexiou C, Hergt R, Halbhuber K J, Kaiser W A and Hilger I 2007 Magnetic nanoparticles as bimodal tools in magnetically induced labeling and magnetic heating of tumor cells: an in vitro study *Nanotechnology* 18 175101/1-9.
[11] Hong X, Gao X and Jiang L 2007 Application of superhydrophobic surface with high adhesive force in no lost transport of superparamagnetic microdroplet *J. Am. Chem. Soc.* 129 1478-9.
[12] Lu A-H, Salabas E L and Schüth F 2007 Magnetic Nanoparticles: Synthesis, Protection, Functionalization, and Application *Angew. Chem. Int. Ed.* 46 1222-44.
[13] Selvan S T, Bullen C, Ashokkumar M and Mulvaney P 2001 Synthesis of Tunable, Highly luminescent QD-glasses through sol-gel processing *Adv. Mater.* 13 985-8.
[14] Trau M and Battersby B J 2001 Novel colloidal materials for high-throughput screening applications in drug discovery and genomics *Adv. Mater.* 13 975-9.
[15] Chan Y, Zimmer J P, Stroh M, Steckel J S, Jain R K and Bawendi M G 2004 Incorporation of luminescent nanocrystals into monodisperse core-shell silica microspheres *Adv. Mater.* 16 2092-7.
[16] Selvan S T, Tan T and Ying J Y 2005 Robust, Non-Cytotoxic, Silica-coated CdSe quantum dots with efficient photoluminescence *Adv. Mater.* 17 1620-5.
[17] Xu H, Cui L, Tong N and Gu H 2006 Development of high magnetization $Fe_3O_4$/polystyrene/silica nanospheres via combined miniemulsion/emulsion polymerization *J. Am. Chem. Soc.* 128 15582-3.
[18] Lu Y, Yin Y, Mayers B T and Xia Y 2002 Modifying the surface properties of superparamagnetic iron oxide nanoparticles through a sol-gel approach *Nano Lett.* 2 183-6.
[19] Salgueiriño-Maceira V, Correa-Duarte M A, Spasova M, Liz-Marzán L M and Farle M 2006 Composite silica spheres with magnetic and luminescent functionalities *Adv. Funct. Mater.* 16 509-14.
[20] Wang D, He J, Rosenzweig N and Rosenzweig Z 2004 Superparamagnetic $Fe_2O_3$ beads-CdSe/ZnS quantum dots core-shell nanocomposite particles for cell separation *Nano Lett.* 4 409-13.
[21] Kim J, Lee J E, Lee J, Yu J H, Kim B C, An K, Hwang Y, Shin C H, Park J G, Kim J and Hyeon T 2006 Magnetic fluorescent delivery vehicle using uniform mesoporous silica spheres embedded with monodisperse magnetic and semiconductor nanocrystals *J. Am. Chem. Soc.* 128 688-9.
[22] Yi D, Selvan S T, Lee S, Papaefthymiou G C, Kundaliya D and Ying J Y 2005 Silica-coated nanocomposites of magnetic nanoparticles and quantum dots *J. Am. Chem. Soc.* 127 4990-1.
[23] Sathe T R, Agrawal A and Nie S 2006 Mesoporous silica beads embedded with semiconductor quantum dots and iron oxide nanocrystals: dual-function microcarriers for optical encoding and magnetic separation *Anal. Chem.* 78 5627-32.
[24] Mamedov A, Belov A, Giersig M, Mamedova N and Kotov N A 2001 Nanorainbows: graded semiconductor films from quantum dots *J. Am. Chem. Soc.* 123 7738-9.
[25] Kagan C R, Murray C B, Nirmal M and Bawendi M G 1996 Electronic energy transfer in CdSe quantum dot solids *Phys. Rev. Lett.* 76 1517-20.
[26] Franzl T, Klar T A, Schietinger S, Rogach A L and Feldmann J 2004 Exciton recycling in graded gap nanocrystal structures *Nano Lett.* 4 1599-603.
[27] Brinker C Y and Scherer G W 1990 *Sol Gel Science: the Physics and Chemistry of Sol-Gel Processing* Academic Press Boston.
[28] Wang Q, Iancu N and Seo D K 2005 Preparation of large transparent silica monoliths with embedded photoluminescent CdSe@ZnS core/shell quantum dots *Chem. Mater.* 17 4762-4.
[29] Wang Q, Xu Y, Zhao X, Chang Y, Liu Y, Jiang L, Sharma J, Seo D K and Yan H 2007 A facile one-step in situ functionalization of quantum dots with preserved photoluminescence for bioconjugation *J. Am. Chem. Soc.* 129 6380-1.
[30] Iancu N, Sharma R and Seo D K 2004 Low-temperature synthetic method for size-controlled CdSe nanocrystals: utilization of boron selenide *Chem. Comm.* 20 2298-9.

[31] Wang Q and Seo D K 2006 Synthesis of deep-red-emitting CdSe quantum dots and general non-inverse-square behavior of quantum confinement in CdSe quantum dots *Chem. Mater.* 18 5764-7.

[32] Van Blaaderen A and Vrij A 1992 Synthesis and characterization of colloidal dispersions of fluorescent, monodisperse silica spheres *Langmuir* 8 2921-31.

[33] Wang Q, Wei Q and Gu H 2003 Preparation of nano $Fe_3O_4$/polystyrene composite microspheres by in situ polymerization *J. Chem. Eng. Jpn.* 36 1227-30.

[34] Wu P, Zhu J and Xu Z 2004 Template-assisted synthesis of mesoporous magnetic nanocomposite particles *Adv. Funct. Mater.* 14 345-51.

[35] Lin Y W, Tseng W L and Chang H T 2006 Using a layer-by-layer assembly technique to fabricate multicolored-light-emitting films of CdSe@CdS and CdTe quantum dots *Adv. Mater.* 18 1381-6.

[36] Gong Y, Gao M, Wang D and Mohwald H 2005 Incorporating fluorescent CdTe nanocrystals into a hydrogel via hydrogen bonding: toward fluorescent microspheres with temperature-responsive properties *Chem. Mater.* 17 2648-53.

We claim:

1. A microstructure comprising
   (a) a core; and
   (b) a plurality of distinct layers surrounding the core; wherein the plurality of distinct layers comprises (i) quantum dot-containing layers, and (ii) spacer layers not containing quantum dots, wherein there are at least two quantum dot containing layers; wherein the quantum dots are present in each quantum dot containing layer at a defined intensity level, wherein each quantum dot containing layer comprises a plurality of a single type of quantum dot that is different relative to quantum dots contained in any of the other quantum dot containing layers, wherein each quantum dot-containing layer is separated from other quantum dot containing layers by a spacer layer, and wherein a ratio of fluorescent intensities from the quantum dots in the plurality of quantum dot containing layers after simultaneous excitation defines a unique barcode for the microstructure.

2. The microstructure of claim 1, wherein the microstructure is between 100 nm and 5 mm in diameter.

3. The microstructure of claim 1 wherein the microstructure is between 100 nm and 2 mm in diameter.

4. The microstructure of claim 1 wherein the microstructure comprises at least four_quantum dot-containing layers.

5. The microstructure of claim 1 wherein the microstructure comprises at least three quantum dot-containing layers.

6. The microstructure of claim 4 wherein the spacer layers are between 10 nm and 500 nm in thickness.

7. The microstructure of claim 1, wherein the quantum dots are covalently embedded in the quantum-dot containing layers.

8. The microstructure of claim 1, wherein the core comprises superparamagnetic material.

9. The microstructure of claim 8, wherein the superparamagnetic material is selected from the group consisting of $Fe_3O_4$ nanoparticles, $Fe_2O_3$ nanoparticles, Mg/Co/Mn doped iron oxide nanoparticles, and FePt nanoparticles.

10. The microstructure of claim 8, wherein the microstructure comprises a spacer layer coated over the core.

11. The method of claim 1, wherein the plurality of distinct layers comprise silica-containing layers.

12. The microstructure of claim 1 wherein the quantum dots are selected from the group consisting of CdS quantum dots, CdSe quantum dots, CdSe@CdS core/shell quantum dots, CdSe@ZnS core/shell quantum dots, CdTe quantum dots, PbS quantum dots, and PbSe quantum dots.

13. The microstructure of claim 1 further comprising one or more probes attached to an outer surface of the microstructure.

14. The microstructure of claim 13 wherein the probe comprises a molecule selected from the group consisting of nucleic acids, proteins, antibodies, polysaccharides, lipids, organic molecules, and inorganic molecules.

15. A molecular recognition system comprising a plurality of different populations of the microstructures of claim 13, wherein each population has a unique bar-code based on the quantum dots present in the microstructure.

16. A method for molecular recognition comprising:
   (a) contacting the molecular recognition system of claim 15 with a test sample under conditions suitable for binding of the one or more probes to a target if present in the test sample;
   (b) removing unbound microstructures;
   (c) detecting fluorescence from microstructures bound to the test sample; and
   (d) identifying presence of one or more targets in the test sample based on a ratio of fluorescence intensity emissions from microstructures bound to the test sample.

17. A method for making the microstructure of claim 1, comprising:
   (a) providing a core;
   (b) coating the core with a plurality of distinct layers, wherein each layer is applied sequentially, wherein the plurality of distinct layers comprises (i) quantum dot-containing layers, and (ii) spacer layers not containing quantum dots, wherein there are at least two quantum dot containing layers; wherein the quantum dots are present in each quantum dot containing layer at a defined intensity level, wherein each quantum dot containing layer comprises a single type of quantum dot that is different relative to quantum dots contained in any of the other quantum dot containing layer, wherein each quantum dot-containing layer is separated from other quantum dot containing layers by a spacer layer, and wherein a ratio of fluorescent intensities from the quantum dots in the plurality of quantum dot containing layers after simultaneous excitation defines a unique barcode for the microstructure.

18. A method for delivering a therapeutic agent to a subject in need thereof, comprising administering the microstructure of claim 1, wherein the core is hollow, and wherein the microstructure comprises a therapeutic agent loaded into the hollow core.

19. A method for delivering a diagnostic agent to a subject in need thereof, comprising administering the microstructure of claim 1, wherein the core is hollow, and wherein the microstructure comprises a diagnostic agent loaded into the hollow core.

20. A method for delivering a contrast agent to a subject in need thereof, comprising administering the microstructure of claim 1, wherein the core is hollow, and wherein the microstructure comprises a contrast agent loaded into the hollow core.

21. A method for delivering an imaging agent to a subject in need thereof, comprising administering the microstructure of claim 1, wherein the core is hollow, and wherein the microstructure comprises an imaging agent loaded into the hollow core.

* * * * *